(12) United States Patent
Mass et al.

(10) Patent No.: US 6,675,045 B2
(45) Date of Patent: Jan. 6, 2004

(54) SPLIT-CAN DIPOLE ANTENNA FOR AN IMPLANTABLE MEDICAL DEVICE

(75) Inventors: William R. Mass, Maple Grove, MN (US); Jeffrey A. Von Arx, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 225 days.

(21) Appl. No.: 09/761,974

(22) Filed: Jan. 16, 2001

(65) Prior Publication Data

US 2002/0095195 A1 Jul. 18, 2002

(51) Int. Cl.$^7$ ............................................. A61N 1/375
(52) U.S. Cl. ........................... 607/32; 607/36; 607/60
(58) Field of Search ........................... 607/30, 32, 36, 607/40, 31, 59; 128/903, 904

(56) References Cited

U.S. PATENT DOCUMENTS

| | | | |
|---|---|---|---|
| 4,230,128 A | 10/1980 | Aramayo | 128/763 |
| 4,556,063 A | 12/1985 | Thompson et al. | 128/419 PT |
| 5,113,869 A | 5/1992 | Nappholz et al. | 128/696 |
| 5,127,404 A | 7/1992 | Wyborny et al. | 128/419 P |
| 5,314,453 A | 5/1994 | Jeutter | 607/61 |
| 5,337,756 A | 8/1994 | Barbier et al. | 128/763 |
| 5,342,408 A | 8/1994 | deCoriolis et al. | 607/32 |
| 5,562,713 A | 10/1996 | Silvian | 607/32 |
| 5,683,432 A | 11/1997 | Goedeke et al. | 607/32 |
| 5,697,088 A | * 12/1997 | Gu | 333/204 |
| 5,697,958 A | * 12/1997 | Paul et al. | 128/901 |
| 5,735,887 A | 4/1998 | Barreras, Sr. et al. | 607/60 |
| 5,861,019 A | * 1/1999 | Sun et al. | 607/36 |
| 5,862,803 A | 1/1999 | Besson et al. | 128/696 |
| 5,957,854 A | 9/1999 | Besson et al. | 600/509 |
| 5,999,857 A | * 12/1999 | Weijand et al. | 128/903 |
| 6,009,350 A | 12/1999 | Renken | 607/32 |
| 6,115,636 A | 9/2000 | Ryan | 607/60 |
| 6,169,925 B1 | 1/2001 | Villaseca et al. | 607/60 |
| 6,252,460 B1 | * 6/2001 | Ito | 330/165 |
| 2002/0042637 A1 | * 4/2002 | Stover | 607/60 |

* cited by examiner

Primary Examiner—George R. Evanisko
(74) Attorney, Agent, or Firm—Schwegman, Lundberg, Woessner & Kluth, P.A.

(57) ABSTRACT

An apparatus and method for enabling far-field radio-frequency communications with an implantable medical device utilizing the device housing as an antenna. Such radio-frequency communications can take place over much greater distances than with inductively coupled antennas.

16 Claims, 2 Drawing Sheets

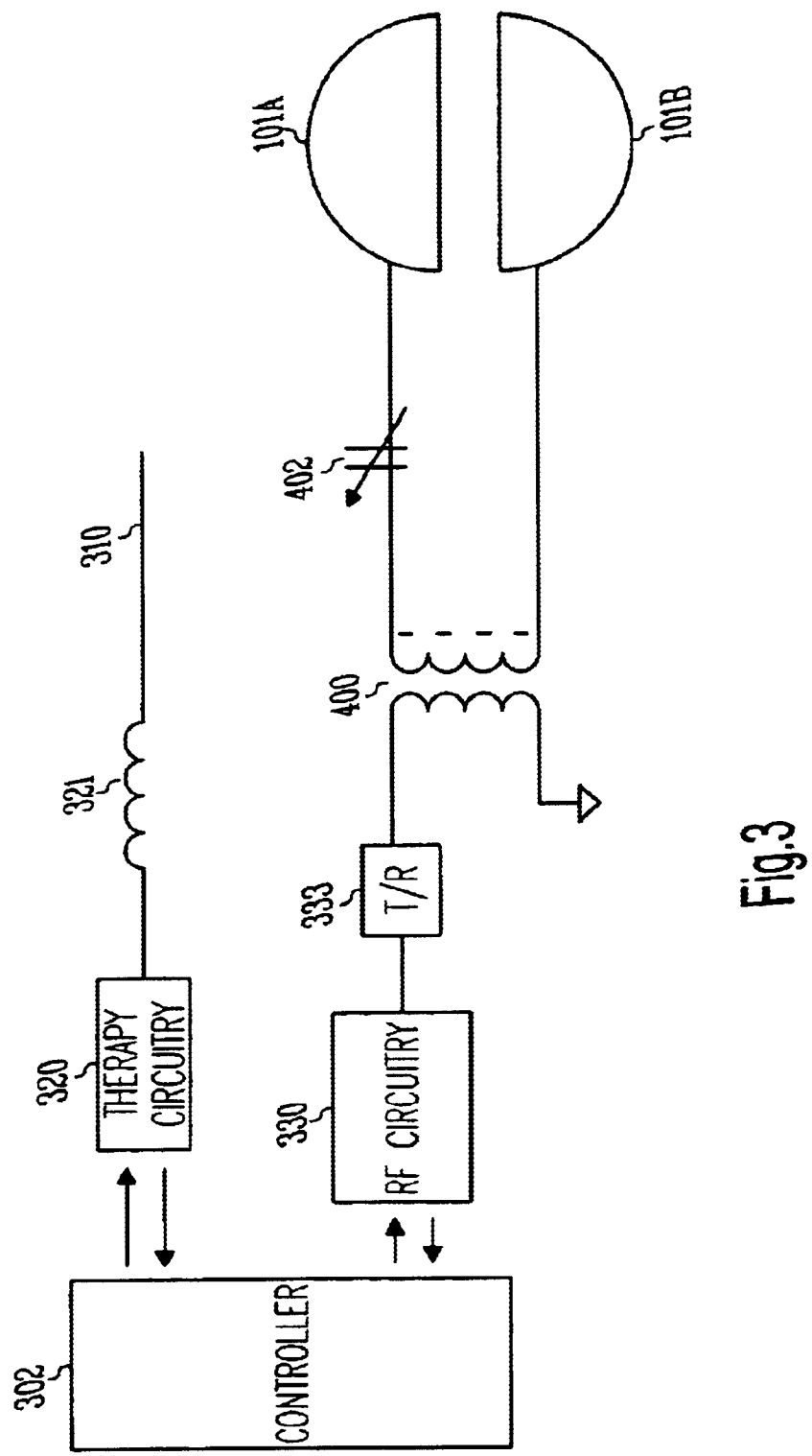

SPLIT-CAN DIPOLE ANTENNA FOR AN IMPLANTABLE MEDICAL DEVICE

FIELD OF THE INVENTION

This invention pertains to implantable medical devices such as cardiac pacemakers and implantable cardioverter/defibrillators. In particular, the invention relates to an apparatus and method for enabling radio-frequency telemetry in such devices.

BACKGROUND

Implantable medical devices, including cardiac rhythm management devices such as pacemakers and implantable cardioverter/defibrillators, typically have the capability to communicate data with a device called an external programmer via a radio-frequency telemetry link. A clinician may use such an external programmer to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data which may typically be telemetered from an implantable device are various operating parameters and physiological data, the latter either collected in real-time or stored from previous monitoring operations.

Telemetry systems for implantable medical devices utilize radio-frequency energy to enable bidirectional communication between the implantable device and an external programmer. An exemplary telemetry system for an external programmer and a cardiac pacemaker is described in U.S. Pat. No. 4,562,841, issued to Brockway et al. and assigned to Cardiac Pacemakers, Inc., the disclosure of which is incorporated herein by reference. A radio-frequency carrier is modulated with digital information, typically by amplitude shift keying where the presence or absence of pulses in the signal constitute binary symbols or bits. The external programmer transmits and receives the radio signal with an antenna incorporated into a wand which can be positioned in proximity to the implanted device. The implantable device also generates and receives the radio signal by means of an antenna, typically formed by a wire coil wrapped around the periphery of the inside of the device casing.

In previous telemetry systems, the implantable device and the external programmer communicate by generating and sensing a modulated electromagnetic field in the near-field region with the antennas of the respective devices inductively coupled together. The wand must therefore be in close proximity to the implantable device, typically within a few inches, in order for communications to take place. This requirement is an inconvenience for a clinician and limits the situations in which telemetry can take place.

SUMMARY OF THE INVENTION

The present invention is an apparatus and method for enabling communications with an implantable medical device utilizing far-field electromagnetic radiation. Using far-field radiation allows communications over much greater distances than with inductively coupled antennas. In accordance with the invention, separate conductive portions of a housing for the implantable device act as a dipole antenna for radiating and receiving far-field radio-frequency radiation modulated with telemetry data. The antenna is dimensioned such that a substantial portion of the radio-frequency energy delivered to it at a specified frequency by a transmitter in the implantable device is emitted as far-field electromagnetic radiation. A tuning circuit may be used to tune the antenna by optimizing its impedance.

BRIEF DESCRIPTION OF THE DRAWINGS

FIG. 3 is a block diagram of the components of an exemplary cardiac rhythm management device.

DETAILED DESCRIPTION

Figure 1:
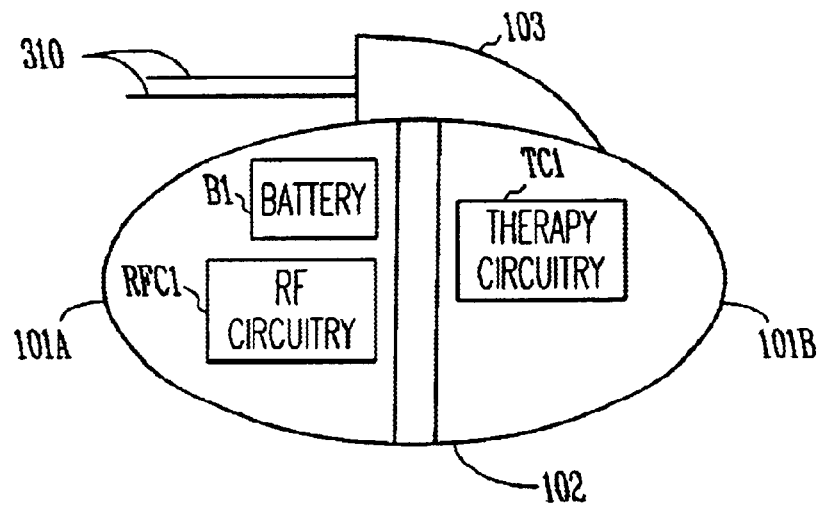
FIG. 1 illustrates one embodiment of a split-can dipole antenna.

As noted above, conventional radio-frequency (RF) telemetry systems used for implantable medical devices such as cardiac pacemakers utilize inductive coupling between the antennas of the implantable device and an external programmer in order to transmit and receive RF signals. Because the induction field produced by a transmitting antenna falls off rapidly with distance, such systems require close proximity between the implantable device and a wand antenna of the external programmer in order to work properly, usually on the order of a few inches. The present invention, on the other hand, is an apparatus and method for enabling telemetry with an implantable medical device utilizing far-field radiation. Communication using far-field radiation can take place over much greater distances which makes it more convenient to use an external programmer. Also, the increased communication range makes possible other applications of the telemetry system such as remote monitoring of patients and communication with other types of external devices.

A time-varying electrical current flowing in an antenna produces a corresponding electromagnetic field configuration that propagates through space in the form of electromagnetic waves. The total field configuration produced by an antenna can be decomposed into a far-field component, where the magnitudes of the electric and magnetic fields vary inversely with distance from the antenna, and a near-field component with field magnitudes varying inversely with higher powers of the distance. The field configuration in the immediate vicinity of the antenna is primarily due to the near-field component, also known as the induction field, while the field configuration at greater distances is due solely to the far-field component, also known as the radiation field. The near-field is a reactive field in which energy is stored and retrieved but results in no net energy outflow from the antenna unless a load is present in the field, coupled either inductively or capacitively to the antenna. The far-field, on the other hand, is a radiating field that carries energy away from the antenna regardless of the presence of a load in the field. This energy loss appears to a circuit driving the antenna as a resistive impedance which is known as the radiation resistance. If the frequency of the RF energy used to drive an antenna is such that the wavelength of electromagnetic waves propagating therein is much greater than the length of the antenna, a negligible far-field component is produced. In order for a substantial portion of the energy delivered to the antenna to be emitted as far-field radiation, the wavelength of the driving signal should not be very much larger than the length of the antenna.

A dipole antenna is made of two lengths of metal, usually arranged end to end with the cable from a transmitter/ receiver feeding each length of the dipole in the middle. An efficiently radiating resonant structure is formed if each length of metal in the dipole is a quarter-wavelength long, so that the combined length of the dipole from end to end is a half-wavelength. A wire antenna for an implantable medical device capable of emitting far-field radiation, however, may require special implantation procedures and may also be broken or deformed as a patient moves resulting in de-tuning. In accordance with the present invention, a dipole antenna for an implantable medical device is formed by separate conductive portions of the device housing or can, referred to herein as a split-can dipole antenna. In one embodiment, the conductive housing is split into two halves separated by an insulating dielectric material, with each half connected to transmitting/receiving circuitry contained within one of the housing portions. Unlike wire antennas, a split-can dipole antenna does not require any special implantation procedures and is a rigid structure which is resistant to breakage or deformation.

An antenna most efficiently radiates energy if the length of the antenna is an integral number of half-wavelengths of the driving signal. A half-wave dipole antenna, for example, is a center-driven conductor which has a length equal to half the wavelength of the driving signal. The natural tuning of a split-can dipole antenna depends, of course on the device size. For example, a typical lengthwise dimension of an implantable cardiac rhythm management device may be about 6.8 cm, which corresponds to a half wavelength of a 2.2 GHz carrier frequency. If each half of a split-can dipole antenna is 3.4 cm, then the antenna is a half-wavelength dipole at that carrier frequency. For medical device applications, carrier frequencies between 300 MHz and 1 GHz are most desirable. As will be discussed below, an antenna tuning circuit may be used to alter the effective electrical length of an antenna by loading it with capacitance or inductance. The split-can antenna is especially advantageous in this respect as compared with conventional wire antennas because it is physically wide and possesses a greater bandwidth. An antenna with a greater bandwidth is easier to tune and is usable over a greater range of frequencies once it is tuned. A larger antenna bandwidth also allows a higher data rate and minimizes the risk of losing communications due to frequency drift.

Figure 2:
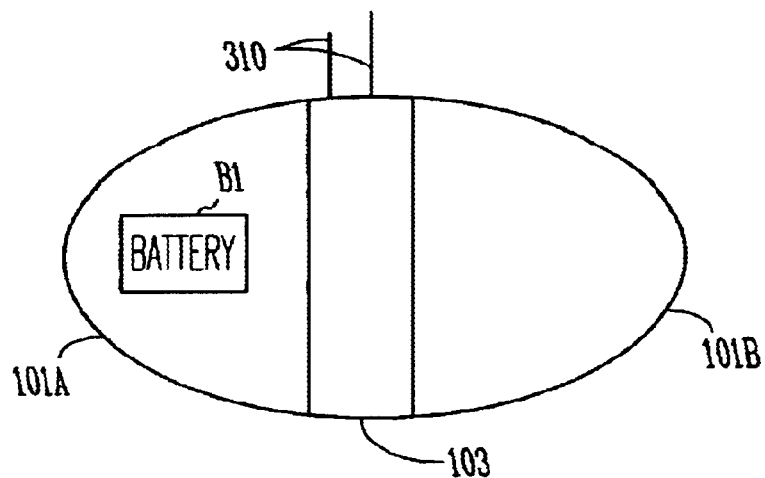
FIG. 2 illustrates an alternate embodiment of a split-can dipole antenna with the device header separating the two housing portions.

FIG. 1 shows an exemplary implantable medical device 100 with a dipole antenna suitable for radiating and receiving far-field electromagnetic radiation formed by respective halves of the device housing 101a and 101b. The device housing is metallic and contains therapy circuitry TC1 for providing particular functionality to the device such as cardiac rhythm management, physiological monitoring, drug delivery, or neuromuscular stimulation as well as circuitry RFC1 for providing RF communications. One or more therapy leads 310 are connected to the therapy circuitry contained within the housing by means of a header 103 with feedthroughs located therein for routing the therapy leads to the appropriate internal components. The two housing portions 101a and 101b are separated by a layer of insulating material 102. FIG. 2 shows an alternate embodiment in which the header is made of dielectric material and is interposed between the two housing portions 101a and 101b, thus also serving to separate the two legs of the dipole antenna. In either embodiment, the two housing portions 101a and 101b are hermetically sealed with a minimum number of feedthroughs between them. A battery B1 is used to supply power to the electronic circuitry within the housing. If the battery alone is contained within one of the housing portions, then only two feedthroughs are needed between the two housing portions, one for each battery terminal. Alternatively, the battery and the RF circuitry can be placed in one housing portion, with the rest of the device circuitry contained in the other portion. This shields the sensitive therapy circuitry from the very noisy RF circuitry.

FIG. 3 is a block diagram of an exemplary implantable cardiac rhythm management device utilizing a split-can dipole antenna for radio-frequency telemetry. In the figure, only one therapy lead 310 is shown but it should be understood that a cardiac rhythm management device may use two or more such leads. A microprocessor controller 302 controls the operation of the therapy circuitry 320 which includes sensing and stimulus generation circuitry that are connected to electrodes by the therapy leads for control of heart rhythm and RF drive circuitry 330 for transmitting and receiving a carrier signal at a specified frequency modulated with telemetry data. The conductors of the therapy lead 310 connect to the therapy circuitry 320 through a filter 321 that serves to isolate the circuitry 320 from any RF signals that may be picked up by the lead. The filter 321 may be a low-pass filter or a notch filter such as a choke. The RF drive circuitry 330 includes an RF transmitter and receiver that are connected by a transmit/receive switch 333 to the dipole antenna formed by the housing portions 101a and 101b. The microprocessor 302 outputs and receives the data contained in the modulated carrier generated or received by the drive circuitry 330.

In this embodiment, the RF drive circuitry 330 is connected to the dipole antenna through an antenna tuning circuit which loads the antenna with a variable amount of inductance or capacitance to thereby adjust the effective electrical length of the antenna and match the antenna impedance to the impedance of the transmitter/receiver. In this manner, the reactance of the antenna may be tuned out so that the antenna forms a resonant structure at the specified carrier frequency and efficiently transmits/receives far-field radiation. The tuning circuit in this embodiment includes a balun transformer 400 and a variable capacitor 402 for loading the antenna with an adjustable amount of reactance. The balun transformer drives the two housing portions 180 degrees out of phase and thus also serves to convert between the single-ended signal generated or received by the transmitter/receiver circuitry and the differential signal generated or received by the antenna. The balun transformer 400 also acts as a high-pass filter which blocks low frequency energy from being passed to the RF circuitry such as may be generated when the housing is used as an electrode in delivering electrostimulation with a monopolar lead.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An implantable medical device, comprising:

therapy circuitry for providing a functionality to the medical device;

RF circuitry for providing RF communications;

a battery for supplying power to the therapy and RF circuitry;

a first housing portion made of conductive material and containing at least part of either the therapy circuitry, the RF circuitry, or the battery;

a second housing portion made of conductive material and containing at least one of the remaining part of either the therapy circuitry, the RF circuitry, or the battery; an insulator electrically separating the first and second housing portions;

wherein the RF circuitry is connected to the first and second housing portions in a manner such that the first and second housing portions form a dipole antenna for transmitting or receiving a modulated radio-frequency carrier at a specified carrier frequency.

2. The device of claim 1 wherein the first and second housing portions are of approximately equal size.

3. The device of claim 1 further comprising a header compartment made of insulating dielectric material and wherein the first and second housing portions are separated by the header compartment.

4. The device of claim 1 wherein the therapy circuitry and the RF circuitry are contained in different ones of the first and second housing portions.

5. The device of claim 3 wherein the battery is contained in one of either the first or second housing portions with the therapy and RF circuitry both contained in the other housing portion.

6. The device of claim 3 wherein the battery and RF circuitry are contained in one of either the first or second housing portions with the therapy circuitry contained in the other housing portion.

7. The device of claim 1 wherein the battery is contained in one of either the first or second housing portions with the therapy and RF circuitry both contained in the other housing portion.

8. The device of claim 1 wherein the battery and circuitry are contained in one of either the first or second housing portions with the therapy circuitry contained in the other housing portion.

9. The device of claim 1 wherein the dimensions of the first and second housing portions are such that a significant portion of radio-frequency energy delivered to the antenna at the specified carrier frequency is emitted as far-field radiation.

10. The device of claim 1 wherein the electrical length of the antenna is approximately one-half wavelength or greater of the radio-frequency carrier at the specified frequency.

11. The device of claim 1 further comprising an antenna tuning circuit electrically connected to the antenna and the RF circuitry for matching the impedance of the antenna to the RF circuitry at a specified carrier frequency by loading the antenna with inductance or capacitance.

12. The device of claim 11 wherein the tuning circuit comprises a balun transformer for converting between a single-ended signal generated or received by the transmitter/receiver circuitry and a differential signal generated or received by the antenna.

13. The device of claim 11 further comprising a variable capacitor connected to the antenna for adjusting the resonant frequency of the antenna.

14. The device of claim 1 wherein the therapy circuitry is rhythm control circuitry and further comprising one or more electrodes connected to the therapy circuitry by therapy leads and adapted for disposition within or near the heart.

15. The device of claim 14 further comprising a filter connected to a therapy lead for blocking radio-frequency signals generated by the RF circuitry from reaching the rhythm control circuitry.

16. The device of claim 15 wherein the filter is a notch filter.

* * * * *